United States Patent [19]

Pyke

[11] Patent Number: 5,591,321

[45] Date of Patent: * Jan. 7, 1997

[54] DETECTION OF FLUIDS WITH METAL-INSULATOR-SEMICONDUCTOR SENSORS

[75] Inventor: Stephen C. Pyke, Sisters, Oreg.

[73] Assignee: Electric Power Research Institute, Palo Alto, Calif.

[*] Notice: The term of this patent shall not extend beyond the expiration date of Pat. No. 5,417,821.

[21] Appl. No.: 442,373

[22] Filed: May 16, 1995

Related U.S. Application Data

[63] Continuation-in-part of Ser. No. 147,002, Nov. 2, 1993, Pat. No. 5,417,821.

[51] Int. Cl.⁶ .................................................. G01N 27/26
[52] U.S. Cl. ......................... 205/787; 205/775; 204/401; 204/412; 204/416; 422/68.1; 422/82.01; 422/82.02; 422/82.03; 324/71.1; 324/71.5; 338/34; 436/144; 436/149; 436/150; 73/31.06
[58] Field of Search ............................. 204/153.1, 416, 204/412, 401; 324/71.1, 71.5; 73/31.06, 23.31, 23.2, 25.03; 422/98, 105, 68.1, 82.01, 82.02, 82.03, 83, 90, 94, 96, 97; 338/34; 436/144, 149, 150

[56] References Cited

U.S. PATENT DOCUMENTS

| | | | |
|---|---|---|---|
| 3,438,738 | 4/1969 | Johnson | 23/232 |
| 3,680,359 | 8/1972 | Lynch | 73/27 |
| 3,719,564 | 3/1973 | Lilly et al. | 204/1 |
| 3,832,600 | 8/1974 | Specht | 371/14 |
| 3,844,160 | 10/1974 | Yamaoka | 73/19 |
| 4,020,830 | 5/1977 | Johnson et al. | 128/2 |
| 4,112,737 | 9/1978 | Morgan | 73/23 |
| 4,180,771 | 12/1979 | Guckel | 324/71 |
| 4,218,298 | 8/1980 | Shimada et al. | 204/195 |
| 4,305,802 | 12/1981 | Koshiishi | 204/195 |
| 4,354,308 | 10/1982 | Shimada et al. | 29/571 |
| 4,368,480 | 1/1983 | Senturia | 357/25 |
| 4,411,741 | 10/1983 | Janata | 204/1 |
| 4,456,522 | 6/1984 | Blackburn | 204/416 |
| 4,486,292 | 12/1984 | Blackburn | 204/416 |
| 4,514,263 | 4/1985 | Janata | 204/1 |
| 4,534,825 | 8/1985 | Koning et al. | 156/644 |
| 4,671,852 | 6/1987 | Pyke | 156/652 |
| 4,714,673 | 12/1987 | Kessler et al. | 435/14 |
| 4,787,958 | 11/1988 | Lytle | 156/652 |
| 4,836,012 | 6/1989 | Dofy et al. | 338/34 |
| 4,931,851 | 6/1990 | Sibbald et al. | 73/31.06 |
| 4,947,104 | 8/1990 | Pyke | 204/416 |
| 4,947,505 | 5/1990 | Sharma et al. | 204/34.5 |
| 4,953,387 | 9/1990 | Johnson et al. | 422/98 |
| 5,055,908 | 10/1991 | Fuller et al. | 357/71 |
| 5,279,795 | 1/1994 | Hughes | 422/98 |
| 5,417,821 | 5/1995 | Pyke | 204/153.1 |

OTHER PUBLICATIONS

M. S. Shiveraman et al, "Hydrogen Sensitivity of Palladuim–Thin Oxide–Silicon Schottky Barriers" Electronic Letters vol. 12, No. 18, pp. 483–484 (Sep., 1976).

Z. Li et al, "A High Sensitivity Solid State Sensor for $H_2$ Detection in Oxygen–Rich Ambients at Room Temperature" IEEE/IEDM–85, pp. 129–132 (1985).

T. L. Poteat, et al "MOS and Schottky Diode Gas Sensors Using Transition Metal Electrodes" Journal of Electronic Materials, vol. 12, No. 1, pp. 181–213 (1983).

Hughes, R. C., et al., Thin Film Palladium and Silver Alloys and layers for metal–insulator–semiconductor sensors, 1074–1083, J. Appl. Phys. 62(3), 1 Aug. 1987.

Primary Examiner—Bruce F. Bell
Attorney, Agent, or Firm—Renner, Kenner, Greive, Bobak, Taylor & Weber

[57] ABSTRACT

A metal-insulator-semiconductor diode sensor having a Pt/Ir alloy and/or a Pt/Sn alloy electrode is sensitive to and can detect ethylene. An array of metal-insulator-semiconductor diode sensors having varying sensitivity responses can indicate a fault in an electrical transformer by the detection of at least one of the key fault gases CO, $H_2$, $C_2H_2$ and $C_2H_4$.

35 Claims, 2 Drawing Sheets

DETECTION OF FLUIDS WITH METAL-INSULATOR-SEMICONDUCTOR SENSORS

CROSS-REFERENCE TO RELATED APPLICATIONS

This application is a continuation-in-part of U.S. Ser. No. 08/147,002, filed Nov. 2, 1993, now U.S. Pat. No. 5,417,821.

TECHNICAL FIELD

The present invention relates in general to methods and devices for the detection of specific components of gases in liquid or gaseous fluid with metal-insulator-semiconductor (MIS) microelectronic sensors. In one embodiment., the invention relates to methods and devices for the detection in oil-filled electrical transformers of specific fault gases using a multisensor array of selective MIS microelectronic sensors.

BACKGROUND OF THE INVENTION

Methods for industrial gas and vapor analysis have evolved along two separate paths. The first involves complex instruments for example infrared spectroscopy, gas chromatography, and mass spectrometry. The development of microcontrollers and microcomputers has led to smaller and more rugged versions of these analytical instruments that were once only found in laboratories. These instruments are very powerful, but they have disadvantages. They are costly and maintenance-intensive. They are usually located far from the gas or vapor source in climate controlled enclosures. The gas or vapor sample is usually transported to the analyzer in a heated tube. This process delay will not provide real time information. These instruments are not likely to be affordable candidates for real-time, in-situ applications such as combustion gas analysis or chemical process analysis. The second evolutionary path is the development of emerging chemical sensor technology.

There are many industrial applications for gas and vapor sensor technology. For example, there is the detection of hazardous gas in the workplace for worker safety, the analysis of products in the combustion of fuel for better control of the air-fuel mixture and the analysis of feed and product streams for the optimization of product yield and waste reduction.

The use of sensors in workplace gas detection instruments is routine. The technologies used are individual sensors which are installed to detect a single gas or vapor whose concentration, in the local environment, may approach a hazardous level. The examples of these gases include hydrogen sulfide, carbon monoxide, chlorine, ammonia, hydrogen, methane and many others.

The development of sensors is ongoing for use in aerospace applications where weight and size are critical issues. For example, the magnitude and location of hydrogen leaks in liquid fueled rockets is important in launch readiness applications.

The use of gas sensors in combustion analysis to control fuel air mixtures began with the use of a solid state electrochemical sensor for oxygen. The sensor was designed to detect the precise air-fuel mixture in automobiles that would not be too rich or too lean.

The use of chemical sensors in chemical process streams has the potential of improving process efficiency and the resulting yield. A direct result of process improvement is the potential to reduce the amount of waste. For example, the water concentration in a silicone process feed stream is an important parameter in the final product quality.

The degree to which these sensors can uniquely identify the gas or vapor they were designed to detect depends on the sensitivity of the sensor to other interfering species and the concentration of those species. The ability to resolve the target gas or vapor is called the selectivity. There are very few examples of sensors which are highly selective (e.g. greater than a ten fold difference in relative sensitivity), and even these do not work ideally. For example, a sensor whose target gas will give an incorrect indication of the target gas when the concentration of the interferant is high enough. In reality, this limitation is relieved by using the sensor in a situation where the situation described above is unlikely.

An additional way to improve the quality of the information provided by a sensor is to process information from an array of sensors.

One application for chemical sensors is in the detection of particular gases in mineral oil-filled electrical transformers. Faults such as arcing, corona discharge, low energy sparking, severely overloading, pump motor failure and overheating in the insulation system can generate hydrogen ($H_2$), acetylene ($C_2H_2$), ethylene ($C_2H_4$), and carbon monoxide (CO) in oil-filled electrical transformers. These conditions can result in transformer malfunction and may eventually lead to failure if not corrected. The detection of the presence of these four transformer fault gases is frequently the first available indication of a possible malfunction. There is a statistical correlation between transformer malfunction conditions and the fault gases they generate. This correlation has enabled the evaluation of possible fault types by a key gas method.

The significant gases (key gases) and the four general fault types with which they are associated are as follows:

a.) Thermal-Oil—$C_2H_4$ b.) Thermal-Cellulose—$CO_2$, CO c.) Electrical Corona—$H_2$ d.) Electrical-Arcing—$H_2$, $C_2H_2$ Because of this correlation, the possible type of fault in a transformer can be evaluated by the analysis of the gases generated in that transformer.

The utility industry has developed various diagnostic theories that employ ratios of certain key gases. The existence of such "gas ratios" makes it possible to improve the reliability of transformers. However, in order to evaluate the possible fault types using the various gas ratios (e.g. Rogers Ratio Method, Doernenburg Ratio), the gases must be distinguished and analyzed.

Currently gas chromatography is used to identify and quantify gases dissolved in oil having a viscosity of 20 centistokes or less at 40° C. (104° F.). A significant disadvantage, to the user, is the lack of real-time analytical information.

For gas chromatography to be effective, the quantity and composition of gases dissolved in oil samples must remain unchanged during transport to the laboratory. Sampling and analysis involves the risk of contamination and operator bias error.

An alternative would be a chemical sensor immersed directly into the oil environment of the electrical transformer, operating on a real-time basis to indicate the presence of an incipient fault, and which would not require sampling the oil and subsequent analysis in a laboratory.

Selective sensors capable of distinguishing and analyzing particular components would exhibit a sensitivity (output/concentration unit) to a particular component that is different in magnitude than the sensitivity to a different component giving a signal.

The sensor response in a mixture of two components should ideally be a simple sum of the response (i.e. voltage) in the individual components. In this linear case, the effects can be resolved conventionally with an analytical algorithm such as one based on matrix algebra as taught by L. W. Potts for chemical analysis in *QuantitativeAnalysis: Theory and Practice,* Harper and Row, New York 1987, Chapter 13.

Chemically sensitive field-effect transistors (CHEMFETs) have been developed for the detection of specific compounds in liquid and gaseous environments, such as the ion sensitive CHEMFETs disclosed in U.S. Pat. No. 4,020,830 to Johnson, et al. and U.S. Pat. No. 4,305,802 to Koshiishi.

Other CHEMFETs have been produced that measure the concentrations of components in a gaseous state, as for example the devices disclosed in U.S. Pat. No. 3,719,564 to Lilly, Jr., et al and described by Shimada, et al. in U.S. Pat. Nos. 4,218,298 and 4,354,308, and the suspended gate field-effect transistors (SGFETs) described by Jiri Janata in U.S. Pat. Nos. 4,411,741 and 4,514,263. These devices are relatively complex and costly to manufacture due to their multiple junctions and diffusion regions.

CHEMFETs in general, and SGFETs in particular are also not well suited to detection of combination of specific compounds or specific compounds in the presence of other potentially interfering chemical species. Combinations of discrete SGFETs with sensitivities to different compounds have been proposed in efforts to address such deficiencies. For example, in U.S. Pat. No. 4,368,480 to Senturia multiplexed CHEMFETs provide logic elements with varying on-off duty cycles. Nevertheless, such combinations are even more difficult and costly to manufacture than individual sensors.

A device and method for detection of fluid concentration utilizing charge storage in a MIS diode is disclosed in U.S. Pat. No. 4,947,104 to Pyke. MIS sensors detect and amplify the change in the work function of its metal electrode when gas adsorbs on its surface. A MIS sensor for hydrogen was described with a palladium metal electrode by M.S. Shiveraman et al, Electron Lett., 12, 483 (1976) and Z. Li et al, IEEE/IEDM-85,125 (1985). MIS sensors with Ni and Pt electrodes for methane and carbon monoxide have been reported by T. L. Poteat, et al J. Electron. Matl., 12,181 (1983).

The MIS tunnel junction was developed with a palladium electrode for hydrogen detection as reported by R. C. Hughes et al, J. Appl. Phys. 62(3), Aug. 1, 1987 (pp 1074–083). It is operated in reverse bias with an oxide layer thin enough for a measurable reverse current. In this example, the work function change is due to a layer of Pd-H dipoles at the metal insulator interface and due to a change in the composition of the metal on adsorbing hydrogen.

It is therefore desirable to provide methods and devices for detecting and analyzing specific gases in a mixture. It is further desirable to provide methods and devices to indicate the presence of the key fault gases in mineral oil, predict their generation rate, and alert the substation operator accordingly.

SUMMARY OF THE INVENTION

The present invention provides an MIS diode sensor having an electrode comprising an alloy of palladium and copper for detecting components in a fluid.

In another embodiment, the present invention provides an MIS diode sensor having an electrode comprising an alloy of platinum and iridium for detecting components in a fluid.

In a further embodiment, the present invention provides an MIS diode sensor having an electrode consisting essentially of iridium for detecting components in a fluid.

In yet another embodiment, the present invention provides an MIS diode sensor having an electrode comprising an alloy of platinum and tin for detecting components in a fluid.

The present invention further provides an MIS diode sensor for detecting acetylene, said sensor having an electrode comprising a composition selected from the group consisting of platinum, platinum/tin alloy, palladium/silver alloy, palladium/copper alloy, palladium/chromium alloy, nickel/chromium alloy, chromium and mixtures thereof.

The present invention further provides an MIS diode sensor for detecting ethylene, said sensor having an electrode comprising a composition selected from the group consisting of platinum/tin alloy, platinum/iridium alloy, palladium/nickel alloy, and mixtures thereof.

The present invention further provides a device for detecting and analyzing at least two selected fluids in a mixture comprising an array of at least two MIS diode sensors including a first MIS diode sensor having a first electrode with a higher sensitivity in a mixture to at least a first fluid and a lower sensitivity in the mixture to at least a second fluid, and a second MIS diode sensor having a second electrode with a higher sensitivity in a mixture to at least the second fluid and a lower sensitivity in the mixture to at least the first fluid. The first electrode has a work function proportional to the concentration of at least the first fluid, producing a corresponding flat-band voltage. The second electrode has a work function proportional to the concentration of at least the second fluid, producing a corresponding flat-band voltage. The device further comprises a circuit for determining the magnitude of the flatband voltage of each sensor, and a processor for calculating at least the first fluid concentration.

The present invention further provides a device for indicating a fault in an electrical transformer comprising an array of at least a first, a second and a third MIS diode sensors, wherein said first sensor has an electrode comprising platinum, said second sensor has an electrode comprising palladium/copper alloy and said third sensor has an electrode comprising palladium/silver alloy. The device further comprises a circuit for determining the magnitude of the flat-band voltage of each sensor in response to the presence of a concentration of a fault gas to which at least one of the sensors is sensitive, and a processor for calculating the fault gas concentration.

In another embodiment, the present invention provides a device for indicating a fault in an electrical transformer containing a fluid wherein the fault is indicated by a concentration of a gas in the transformer fluid, comprising an array of a plurality of metal-insulator-semiconductor diode sensors having electrodes, wherein the electrode of a first sensor has a first sensitivity to a first target gas and wherein said first sensitivity is different than sensitivities of the first sensor to other target gases in the transformer fluid.

In a preferred embodiment of this device, the sensitivity of at least one sensor to said first target gas is different than the sensitivities of other electrodes in the array to said first target gas. Preferably, each said sensor has a sensitivity to at least one target gas which is different than the sensitivity of each other said sensor to said at least one target gas. The device further comprises a circuit for determining the relative magnitude of the flat-band voltage of each sensor in response to the presence of the target gas, and a processor for resolving the concentrations of the target gases. The device may include an indicator for communicating the concentrations of the target gases.

In a preferred embodiment, the present invention provides a device for indicating a fault in an electrical transformer comprising an array of at least a first, a second, a third, a fourth and a fifth metal-insulator-semiconductor diode sensor, wherein the sensors each independently have an electrode which comprises a metal selected from the group consisting of platinum, palladium/silver alloy, palladium/copper alloy, platinum/iridium alloy, platinum/tin alloy, and palladium/nickel alloy.

The present invention provides a method for detecting at least one component in a fluid utilizing a metal-insulator-semiconductor diode sensor, wherein said at least one component is selected from the group consisting of carbon monoxide, hydrogen, acetylene, ethylene and mixtures thereof, comprising: providing said sensor having an electrode comprising an alloy of platinum and iridium, contacting the electrode with the fluid, and measuring the sensitivity of the electrode to said at least one component in the fluid. The method is capable for detecting components in an oil phase, such as a transformer mineral oil.

In a preferred embodiment, the present invention provides a method for detecting ethylene in a fluid utilizing a metal-insulator-semiconductor diode sensor, comprising: providing said sensor having an electrode comprising a composition selected from the group consisting of platinum, platinum/iridium alloy, platinum/tin alloy, palladium/nickel alloy, and mixtures thereof, contacting the electrode with the fluid, and measuring the sensitivity of the electrode to ethylene. The method is capable for detecting ethylene in an oil phase, such as a transformer mineral oil.

DETAILED DESCRIPTION OF THE INVENTION

A device in accordance with the present invention for monitoring the concentration of at least one selected fluid, such as an electroactive gas, includes a metal insulator semiconductor diode sensor having a work function ($\Phi_{MS}$) difference proportional to the selected fluid concentration and a flat-band voltage ($V_{fb}$), proportional to the work function. Circuitry is provided for determining the magnitude of the change in $V_{fb}$ from which the change in the selected fluid concentration may be calculated.

Figure 1:
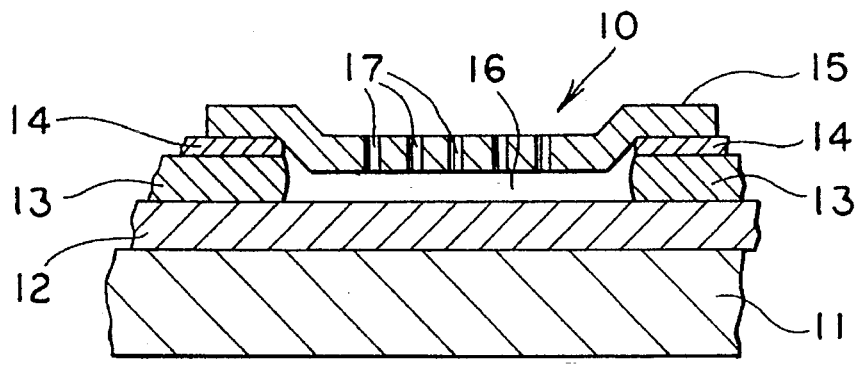
FIG. 1 is an elevational view through an exemplary metal insulator semiconductor diode embodying the concepts of the present invention.

FIG. 1 illustrates a device generally indicated by the numeral 10, which also embodies a method for monitoring the concentration of at least one selected liquid or gaseous fluid. Device 10 is and shall hereinafter be referred to as a metal insulator semiconductor (MIS) diode.

MIS diode 10 may be formed of a semiconductor substrate 11 having p or n type doping characteristics, a layer of dielectric, or insulator 12 such as silicon dioxide and/or silicon nitride covering substrate 11 and sacrificial layers 13 and 14 applied to the surface of insulator 12 opposite substrate 11. Sacrificial layers 13 and 14 may be made respectively of a fugitive metallic material such as a thin film of aluminum and tungsten/titanium, or other conventional sacrificial materials such as tungsten, chromium, glass or organic materials. The fugitive sacrificial layer 13 and thin film sacrificial layer 14 are etched or otherwise formed to provide a cavity 16 into which the selected fluid may flow after passage through a plurality of holes 17 in suspended catalytic electrode 15. In use, the selected fluid, such as electroactive gas, adsorbs onto the electrode, inducing the responsive change in flat-band voltage.

Substrate 11 may alternatively be comprised of a semiconductor such as gallium arsenide, indium phosphide or titanium dioxide, and insulator 12 may be comprised of alumina, silicon nitride or aluminum nitride. A further alternative embodiment and its fabrication will be described with regard to FIG. 1A, below.

Where greater noise immunity, redundancy, or ability to detect combinations of specific components or specific components in the presence of other potentially interfering chemical species is desired, it is preferable to integrally form a plurality of MIS diodes in an array together with suitable circuitry to selectively determine the contribution to Vfb for each component of the mixture.

A plurality of metal insulator semiconductor diodes, each of whose work function is variously proportional to each of the selected fluid component concentrations and whose $V_{fb}$ is proportional to the concentrations, may be connected to a microprocessor for later computing each of the component concentrations.

Figure 2:
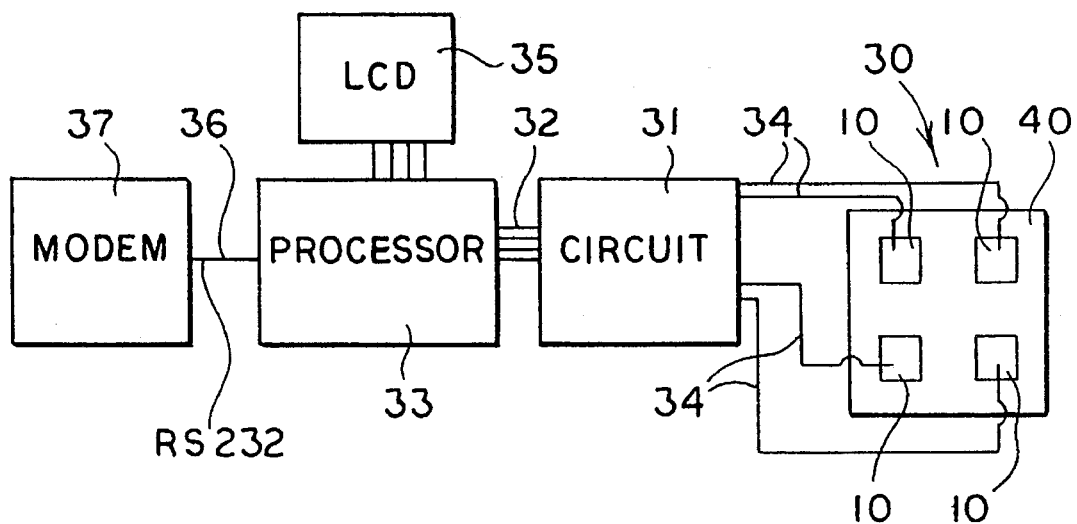
FIG. 2 is a plan view of a portion of an array of metal insulator semiconductor diodes embodying the concepts of the present invention and corresponding circuitry.

As depicted in FIG. 2, each MIS diode 10 which forms a part of array 30 is electronically connected to an analog circuit 31 for analog-to-digital conversion, by wire conductors 34. The array 30 may be mounted on an alumina substrate 40 to control temperature and provide for electrical isolation. Fluid concentrations are calculated from the digital signal relayed through electrical pathway 32 using a matrix-based algorithm installed in a microprocessor 33, such as a Motorola HCll microprocessor. The real-time gas concentration is communicated by an indicator, such as being displayed on a liquid crystal display 35 and/or being made available through an RS232 or fiber optic connection 36 for remote access such as by modem 37. Each MIS diode 10 may be provided with suspended electrode materials suitable for sensitivity to a desired fluid. In this manner a multiple gas and/or improved reliability detector may be achieved.

It should be noted that the MIS diode sensors described herein can operate either in the gas phase or immersed in a liquid such as mineral oil, and do not require an electrolyte or oxygen for operation.

In one embodiment of the invention, the composition of the suspended electrode 15 is provided which is selective in its response to a component fluid, or fault gas, indicative of the condition of the electric transformer. In a preferred embodiment of the invention, a combination of suspended electrode compositions is utilized in an array of associated MIS diodes, resulting in a more reliable measurement of each of the gases. This is due to the electrode compositions exhibiting varying sensitivity to more than one component fluid, or fault gas, in the fluid mixture, or oil. If each of the electrode compositions were sensitive to only a particular component fluid, or gas, the reliability of the measurement would be solely dependent upon each individual sensor. When MIS diode sensors having different electrode compositions are utilized in an associated array, each sensor can be used as a check on the other(s).

In an exemplifying embodiment of the invention, MIS diode sensor electrode compositions selected for individual transformer faults and their corresponding symptomatic gases, and more preferably for use in an associated array are listed in Table I. These sensor electrode compositions are not affected by, and thus do not respond to saturated hydrocarbons, carbon dioxide or nitrogen. Any sensitivity to the transformer mineral oil would provide a constant effect or a slowly changing background which would be calibrated out of the measurement.

The etched wafers were sawed and cleaved. Individual sensor die were secured and contacted electrically to headers with silver epoxy.

In an alternative embodiment, aluminum can be utilized rather than TiW. In that instance, an etch process in PNA (1,600 ml $H_2O$, 100 ml phosphoric acid, 100 ml nitric acid, and 100 ml acetic acid, diluted 25:1 with water) removes the aluminum from underneath the electrode.

EXAMPLE 1

An automated vapor dilution and delivery system (VG7000, Microsensor System, Inc.) was used to introduce test gases to the electrodes. The system was programmed to switch between sources of analyzed target gas diluted in nitrogen (AIRCO Special Gases; Division of BOC, Inc.) and pure nitrogen. The sensors were tested at between 50° and 100° Centigrade in an environmental chamber (Ransco 900

TABLE I

| FAULT TYPE | PRINCIPAL GAS | PRINCIPAL ELECTRODE COMPOSITION |
|---|---|---|
| Overheated Oil | $C_2H_4$, $H_2$ (Also $C_2H_6$, with smaller quantities of $H_2$ and $CH_4$ may form. Traces of $C_2H_2$ may form if fault is severe or involves electrical contacts.) | Platinum |
| Overheated Cellulose | CO (Also, $C_2H_6$ and $C_2H_4$ may form if fault involves oil-impregnated structure.) | Palladium/Copper |
| Corona | $H_2$ (Also $CH_4$, $C_2H_6$ and $C_2H_4$. Comparable amounts of CO and $CO_2$ may result from discharges in cellulose.) | Palladium/Silver |
| Arcing | $H_2$, $C_2H_2$ (Also, $CH_4$, $C_2H_6$ and $C_2H_4$. CO and $CO_2$ may form if the fault involves cellulose. Oil may be carbonized.) | Platinum |

The fabrication and testing of microelectronic MIS diode sensors having electrodes including the above compositions for target key fault gases are described below.

Fabrication

Figure 1A:
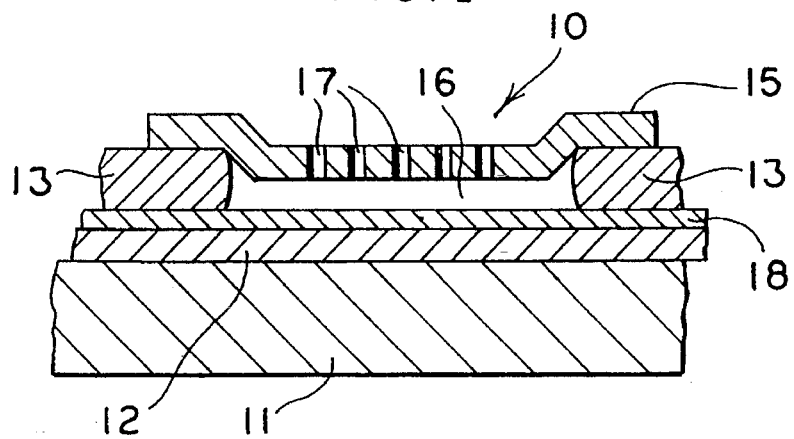
FIG. 1A is an elevational view through an alternative embodiment of the inventive metal insulator semiconductor diode.

Alternative embodiment MIS diodes, having the structure shown in FIG. 1A were fabricated as follows. The sensor wafer fabrication process began with a p-type silicon substrate 11. The substrate 11 was cleaned in HF, and a 300 Å silicon oxide insulator layer 12 was grown in $O_2/N_2$ at high temperature. Separate field oxide and gate oxide zones may be formed if desired, to reduce noise by isolating the column of silicon under the electrode.

A 500 Å isolation layer 18 of $Si_3N_4$ was deposited on the oxide by a low pressure chemical vapor deposition (LPCVD) process. A lift-off photoresist was deposited, exposed and developed. A sacrificial layer 13 of titanium tungsten alloy (200 Å) was sputtered onto the silicon nitride isolation layer 18 to provide a satisfactory bonding surface for adhesion of the deposited noble metal electrode 15. The photo-resist was dissolved to lift off the unwanted electrode material and resolve the electrode 15 and hole 17 patterns.

The wafers were etched in a solution of 0.1 moles per liter EDTA held at a pH=9.5 to 10.5 at room temperature for 5–10 minutes. The etch removes the TiW to form cavity 16. With this process the adhesion to the nitride layer was achieved by metal columns that were not completely etched.

series, Despatch, Inc.), where the sensors (on TO-8 headers) were pressed into a Vespel™ (DuPont) test fixture with low dead volume. Temperature conditioning of the feed gas (100 standard cubic centimeters per minute) was achieved by flowing gas through a one-meter length of ¼-inch diameter copper coil inside the environmental chamber prior to exposure to the sensor.

A microelectronic MIS diode sensor having an electrode composition of platinum (Pt) was coated with mineral oil and sequentially exposed to hydrogen ($H_2$), acetylene ($C_2H_2$), ethylene ($C_2H_4$), and carbon monoxide (CO) in a nitrogen ($N_2$) carrier gas. This sensor test demonstrated that the Pt electrode was responsive to $H_2$, $C_2H_2$ and $C_2H_4$, and more importantly, that the signal emitted by the Pt electrode sensor clearly distinguished the three gases from carbon monoxide (CO).

The sensitivity (volts/ppm) of each of the suspended catalytic electrodes was determined by exposing each of the sensors to increasing concentrations of each of the key gases. In a typical experiment, the concentration was held at 1 ppm in a background of nitrogen for 15 minutes to one hour. The temperature was held constant. The sensor was allowed to reach equilibrium at constant concentration during which time the voltage output was recorded. The concentration was increased, and the experiment was repeated. The sensitivity proved to be linear in the log of the concentration (ppm) over the ranges of interest for the analysis of the key gases.

It is preferred that the MIS sensor electrodes which are to be used to detect acetylene or ethylene be exposed to hydrogen or a similar reductant after exposure to air or oxygen, in order to remove adsorbed oxygen from the electrode surface. An exposure to hydrogen at a dose rate of about 1 ppm·hour was found sufficient for most electrode compositions to react with adsorbed oxygen to form water, which was then desorbed from the electrode metal surface.

Figure 3:
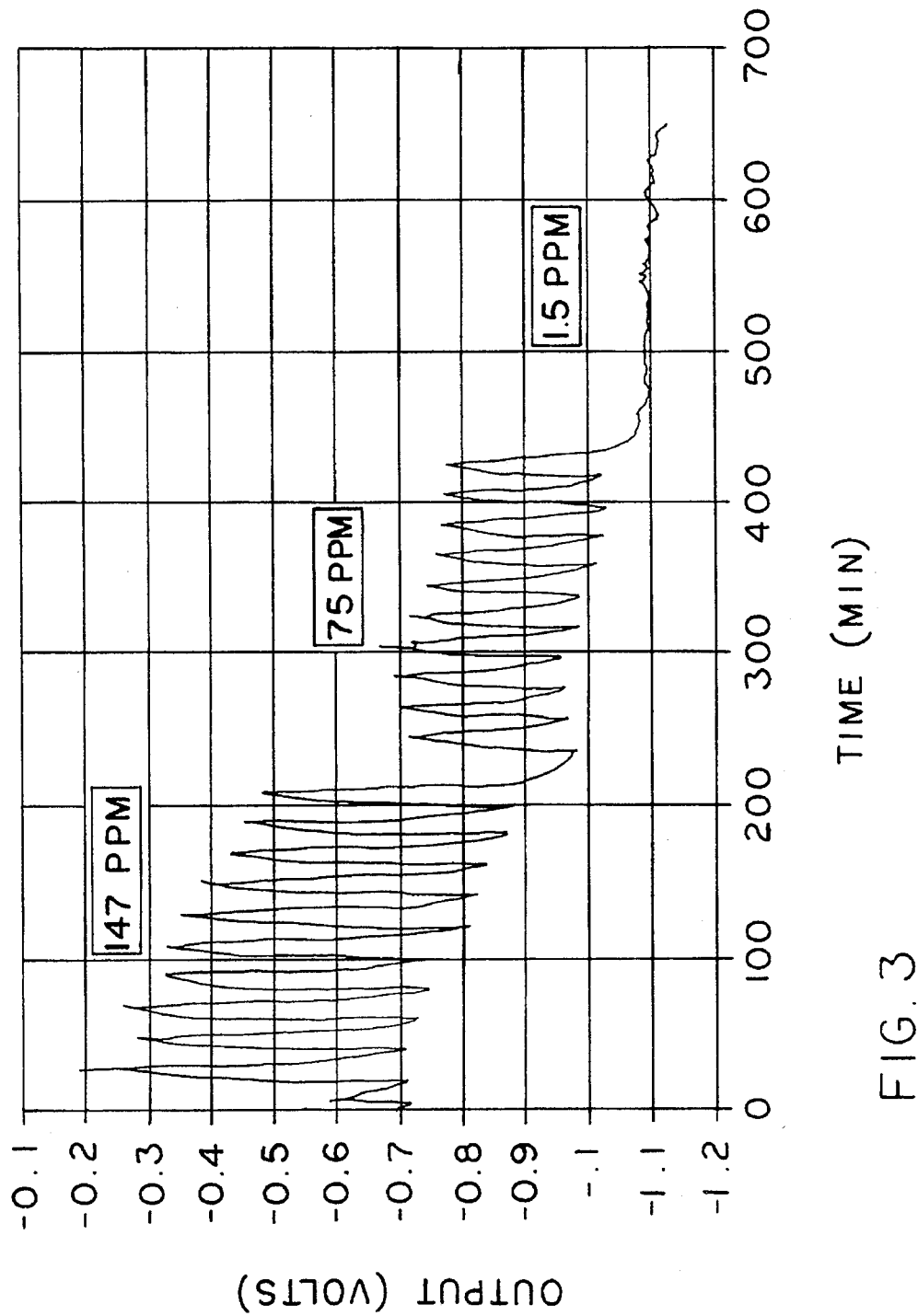
FIG. 3 is a graphical representation of the response to hydrogen of a platinum electrode MIS sensor in mineral oil.

In the example of platinum responding to the key gases at 60 degrees centigrade, the sensitivity to hydrogen was 2.5 times greater than to either acetylene or ethylene and at least 10 times greater than to carbon monoxide in the concentration ranges of interest. An example of the response to hydrogen at 3 different concentrations of a platinum electrode MIS sensor is represented by the graph shown in FIG. 3.

A comparison of the selectivity and sensitivity of Pt electrode sensors to the various target gases is shown in Table II below. It is theorized that the effect on the magnitude and sign of the output are proportional to the strength and polarity of the electrode to component bond.

TABLE II

| Target Gas | Platinum MIS |
|---|---|
| Hydrogen | 100 |
| Carbon Monoxide | <10 |
| Acetylene | 40 |
| Ethylene | 40 |

Using four or more sensors with electrodes of varying composition, the sensitivities to the various key gases were found to vary such that in combination, in an analysis algorithm as referred to above, the composition of each of the key gases can be computed. In one example, a system of linear equations can be used to compute the concentrations. In a preferred embodiment, a matrix formulation of the sensitivities is combined with experimentally determined constants to compute the concentrations. Any other formulation of algorithm to compute the concentrations from the inputs of variously sensitive MIS sensors or CHEMFETS with catalytic suspended electrodes could also be used.

EXAMPLE 2

A microelectronic MIS diode sensor having an electrode composition of an alloy (about 50 atomic percent) of palladium and copper (Pd/Cu) was tested for its response in oil to carbon monoxide (CO) at a level of 2000 ppm in nitrogen. The Pd/Cu electrode sensor responded to that CO concentration with an output of 800 millivolts (mV) at 100° C.

In the Pd/Cu electrode sensor, we have found that hydrogen sensitivity is less than 10% of the sensitivity to CO. The Pd/Cu electrode sensor thus exhibited the selectivity necessary to identify and quantify CO in mixtures containing $H_2$. The Pd/Cu sensor responded with greater sensitivity to CO than it did to the other key fault gases.

The MIS diode sensor having a palladium/copper electrode demonstrated a response, although with different sensitivities, to hydrogen, carbon monoxide, and unsaturated gaseous hydrocarbons such as ethylene and acetylene. Such a Pd/Cu electrode sensor could be used as a detector for any of these fluids in a system where the other listed response-inducing fluids are absent, or where the other fluids' presence and concentration are detectable and calculable using a different sensor (as a reference). The preferred atomic ratios of the components of the Pd/Cu alloy range from about 1Pd:3Cu to about 3 Pd:1Cu.

EXAMPLE 3

A microelectronic MIS diode sensor having an electrode composition of an alloy about 25 atomic percent of palladium and silver (Pd/Ag) was tested for its response to target fault gases. In the test of palladium/silver response to the key gases at 60 degrees centigrade, the sensitivity to hydrogen was about 1.2 times greater than to acetylene and about 1.4 times greater than to ethylene, and at least 10 times greater than to carbon monoxide in the concentration ranges of interest.

Alternative Embodiments

For electrical transformer fault gases, the key gas concentrations in the following ranges were tested with various MIS electrode compositions to determine response.

| Hydrogen | 3–3,000 ppm |
|---|---|
| Acetylene | 1–150 ppm |
| Ethylene | 3–300 ppm |
| Carbon Monoxide | 20–2,000 ppm |

In a preferred embodiment, an array of three MIS diode sensors was fabricated each having a different electrode composition from Table I. In addition to the different associated sensors distinguishing both different and some similar gases and thus being able to serve as references for one another, the range of selectivity is improved with different sensors having different sensitivity to the same gas, and reliability is improved.

Alternative MIS diode electrode compositions which are responsive to and selective for key fault gases are listed below in Table III.

TABLE III

| PRINCIPAL GAS | ELECTRODE COMPOSITION |
|---|---|
| $C_2H_4$ | Platinum/Tin |
|  | Palladium/Silver |
|  | Palladium/Copper |
| CO | Nickel/Chromium |
|  | Palladium/Silver |
| $H_2$ | Platinum |
|  | Palladium/Nickel |
|  | Palladium/Chromium |
|  | Palladium/Copper |
| $H_2$, $C_2H_2$ | Chromium |
|  | Platinum/Tin |
|  | Palladium/Copper |
|  | Palladium/Silver |
|  | Palladium/Chromium |
|  | Nickel/Chromium |

We have found that an MIS diode sensor having a platinum/iridium alloy electrode is sensitive to the key target gases, and that its sensitivity to all four above noted fault gases in a fluid is of sufficient magnitude to permit it to be utilized in an array to resolve the individual fault gases and their concentrations. The selectivity of the platinum/iridium alloy electrode is such that ethylene is a principal gas which may be detected and resolved by a sensor containing a Pt/Ir alloy electrode.

By "sensitive" is meant that the subject electrode's response is proportional to the concentration of the target gas, and its response to that gas is high enough to overcome background "noise" and permit resolution of the concentration of the gas in a mixture, particularly when another electrode or electrodes are used in an array to resolve other gases in the mixture to which the subject electrode is also sensitive.

Resolution of ethylene is improved in mixtures of gases in a fluid, using an MIS diode sensor array having a sensor electrode of a Pt/Ir alloy, particularly when at least one sensor in the array has another metal electrode acting as a reference for Pt/Ir electrode. Preferred Pt/Ir alloys include those having an atomic percent of iridium of about 5% to about 90%, most preferably about 30% iridium (Pt30Ir). An MIS diode sensor having an electrode consisting essentially of iridium can also detect selected components in a fluid.

Other metal electrodes of MIS diode sensors which we have found to exhibit selective sensitivity to ethylene include platinum, platinum/tin alloy, palladium/nickel alloy and mixtures thereof. Examples of such alloys include but are not limited to Pt50Sn (50 at % tin), Pd25Ni (25 at % nickel), and Pd50Ni (50 at % nickel). According to the invention, therefore, a method is provided for detecting ethylene in a fluid utilizing a metal-insulator-semiconductor diode sensor comprising providing said sensor having an electrode comprising a composition selected from the group consisting of platinum, platinum/iridium alloy, platinum/tin alloy, palladium/nickel alloy, and mixtures thereof, contacting the electrode with the fluid, and measuring the sensitivity of the electrode to ethylene. The electrode may conveniently be contacted by the fluid by placing or locating the electrode in the fluid.

MIS diode sensors having electrodes comprising alloys of platinum and tin are useful in detecting components in a fluid, preferably those comprising about 5% to about 80% tin.

The selectivity responses of various MIS diode sensor electrode compositions were screened and tested in the gas phase at 100° C. The sensitivities of the electrodes are listed in TABLE IV A, reported as millivolts per each factor of 10 increase in concentration of the target gas (mV/decade). The larger the absolute value of the millivolts, the greater the sensitivity of the electrodes.

TABLE IV A

SENSOR SELECTIVITY RESPONSE
(mV/decade at 100° C.)

| Composition | Hydrogen | Acetylene | Ethylene | Carbon Monoxide |
|---|---|---|---|---|
| Pd50Ni | −125 | −30 | −35 | −25 |
| Pd25Ni | −100 | −200 | 35 | 100 |
| Ni | 0 | 5 | 0 | 0 |
| PdCu | −200 | −190 | 0 | −60 |
| PdAg (1) | −90 | −200 | 150 | −150 |
| PdAg (2) | −120 | −135 | 10 | −15 |
| PdAg (3) | −190 | −20 | 30 | −100 |
| Pt (4) | −175 | −45 | −65 | −80 |
| Pt (5) | −110 | −180 | −80 | −225 |
| PtIr | −195 | −90 | 30 | −130 |
| PtSn | −950 | −5 | −20 | 0 |

Variations in the MIS diode sensors marked (1) through (5) are detailed in Table IV B.

TABLE IV B

| Sample | Back Surface | Back Electrical Contact | Dielectric Thickness | Sacrificial Layer |
|---|---|---|---|---|
| PdAg - (1) | Removed Si3N4 | CrAu alloy | 1,000 Å | None |
| PdAg - (2) | Blocking | Ag epoxy | 1,000 Å | None |
| PdAg - (3) | Blocking oxide/nitride oxide/nitride | Ag epoxy | 1,500 Å | TiW |
| Pt - (4) | Removed Si3N4 | CrAu alloy | 1,500 Å | Cr |
| Pt - (5) | Plasma etch | CrAu alloy | 1,500 Å | TiW |

The composition of the Sn alloy of Table IV A contained 50 at % Sn (Pt50Sn). The Ir alloy of Table IV A contained 30 at % Ir (Pr30Ir). All PdAg alloy wafers were 26 at % Ag (Pd26Ag).

In addition to the two palladium/nickel alloys (50 at % Ni and 25 at % Ni), palladium/silver and platinum, alloys of platinum/iridium and platinum tin were found to be responsive to ethylene. MIS diode sensors having an electrode comprising at least one of these metal electrodes can be used in a device and method for detecting ethylene by contacting the electrode with the fluid potentially containing ethylene, and measuring the sensitivity of the electrode to the ethylene.

The nickel electrode tested in Table IV A did not exhibit a response to hydrogen, ethylene or carbon monoxide. Not being sensitive to these components, a sensor having a nickel electrode may be used as a temperature reference electrode in the system. Another metal suitable for use as temperature reference electrode is gold, although it has exhibited a slight reactivity to hydrogen.

Based on the sensitivity results of Table IV A, arrays of various combinations of five (5) MIS sensors are listed in Examples 4–7 of Table V, spanning the range of sensitivities to ethylene. The relative response of four arrays determined by singular value decomposition matrix analysis are listed in Table V. It is generally preferred to use the combination exhibiting the best response for the weakest response gas, namely ethylene.

Selection of a particular combination of electrode compositions for a particular application may, however, involve a tradeoff between optimum sensitivities to particular expected target gases, temperature effects, and long term stability considerations for selected compositions. Those skilled in the art can determine preferable combinations of electrodes for arrays which meet the criteria imposed by the particular application.

TABLE V

FIVE SENSOR ARRAY RELATIVE RESPONSE
(100° C.)

| Example | 4 | 5 | 6 | 7 |
|---|---|---|---|---|
| Sensor | Pt | Pt | Pt | Pt |
| Sensor | Pd25Ni | Pd25Ni | PdCu | PdCu |
| Sensor | PdCu | Pd50Ni | PdAg(1) | PdAg(1) |
| Sensor | PdAg(1) | PtIr | PdAg(2) | PdAg(3) |
| Sensor | PdAg(3) | PtSn | PtSn | PtIr |
| H2 | 568 | 1006 | 1021 | 534 |
| C2H2 | 180 | 292 | 377 | 176 |
| CO | 150 | 87 | 175 | 173 |
| C2H4 | 4 | 58 | 111 | 116 |

Although the array of Example 7 exhibits the best absolute value response for ethylene, there is better sensitivity to acetylene in the array of Example 6. The array of Example 5 is a preferred combination, due to the greater high temperature stability of the metal electrodes used. These arrays are suitable for use in a device for indicating a fault in an electrical transformer, as detailed above. The device preferably includes a circuit for determining the magnitude of the flat-band voltage change of each sensor in response to a change in concentration of a gas, as well as a processor for calculating the concentration of each gas.

As the number of sensors on an array is increased, the signal to noise ratio is increased by the square root of the number of sensors. In addition to the desire to optimize the signal to noise ratio, there are considerations of space and geometry for the number of sensors that can fit on an array without adversely affecting detection and sensitivity. Ideally, the number of sensors utilized is optimized based on the surface area of metal required for sensitivity, and the number of sensors required to resolve the target gases.

Table VI reports the sensitivities of the electrode metals listed, tested in the gas phase at 60° C. for screening purposes, as in Table IVA above. The sensitivity is less at 60° C. than at 100° C. Variations in the electrodes are described in Table, IVB above.

TABLE VI

SENSOR SELECTIVELY RESPONSE
(mV/decade AT 60° C.)

| Composition | Hydrogen | Acetylene | Ethylene | Carbon Monoxide |
|---|---|---|---|---|
| Pd50Ni | −150 | −30 | −20 | −35 |
| Pd25Ni | −90 | −30 | −20 | −10 |
| Ni | 0 | 0 | 0 | −5 |
| PdCu | −120 | −150 | 0 | 5 |
| PdCu | −200 | −90 | 0 | 0 |
| PdCu | −165 | −175 | 0 | 0 |
| PdAg (1) | −140 | −75 | 0 | 0 |
| PdAg (2) | −170 | −150 | 0 | 15 |
| PdAg (3) | −175 | −210 | 0 | 20 |
| Pt | −120 | −70 | −25 | 15 |
| PtIr | −195 | −5 | −20 | 0 |
| PtSn | −750 | −15 | −30 | −150 |

In Table VII, arrays of various combinations of five (5) MIS diode sensors are listed in Examples 8–11, based on the sensitivities listed in Table VI. Each of the four key target gases, hydrogen, acetylene, carbon monoxide and ethylene, may be resolved, as in Examples 4–7 above.

TABLE VII

FIVE SENSOR ARRAY RELATIVE RESPONSE
(60° C.)

| Example | 8 | 9 | 10 | 11 |
|---|---|---|---|---|
| Sensor | Pt | Pt | Pt | Pt |
| Sensor | Pd25Ni | Pd25Ni | Pd25Ni | Pd50Ni |
| Sensor | PdCu | PdCu | PdCu | PdAg |
| Sensor | PdAg | PtIr | PdAg | PdIr |
| Sensor | PtIr | PtAg | PtSn | PtSn |
| H2 | 392 | 762 | 753 | 781 |
| C2H2 | 131 | 173 | 220 | 163 |
| CO | 240 | 46 | 23 | 44 |
| C2H4 | 8 | 19 | 19 | 24 |

According to the invention, the electrode composition of at least one of the sensors within the array can be varied to maximize selectivity to a particular, selected component in the mixture of components potentially present in the fluid for detection. For example, the array of Example 8 maximizes selectivity to carbon monoxide, the array of Example 10 maximizes selectivity to acetylene, and the arrays of Examples 9 and 11 maximize selectivity to ethylene.

The sensitivity responses of five (5) metals were tested in the oil phase at 60° C., as reported in Table VIII. Further metals, such as palladium copper alloys, would also be suitable for use in the oil phase system. The key target gases can be resolved in this system, which would be encountered in mineral oil-containing electrical transformers.

TABLE VIII

SENSOR SENSITIVITY RESPONSE IN OIL-PHASE
(mV/decade at 60° C.)

| Composition | Hydrogen | Acetylene | Ethylene | Carbon Monoxide |
|---|---|---|---|---|
| Pt | −450 | 10 | −19 | 17 |
| Pd25Ni | −186 | 87 | 7 | 27 |
| PdAg | −164 | 90 | 53 | 9 |
| PtIr | −576 | 42 | −19 | 77 |
| PtSn | −374 | −58 | −20 | −69 |

A device for indicating a fault in an electrical transformer containing a fluid can thus be provided, wherein the fault is indicated by a concentration of a gas in the transformer fluid, the device comprising an array of a plurality of metal-insulator-semiconductor diode sensors having electrodes, wherein the electrode of a first sensor has a first sensitivity to a first target gas and wherein said first sensitivity is different than sensitivities of the first sensor to other target gases in the transformer fluid.

In a preferred embodiment of this device, the sensitivity of at least one sensor, most preferably the first sensor, to said first target gas is different than the sensitivities of other electrodes in the array to said first target gas. Preferably, each said sensor has a sensitivity to at least one target gas which is different than the sensitivity of each other said sensor to said at least one target gas.

The device further comprises a circuit for determining the magnitude of the flat-band voltage of each sensor in response to the presence of the target gas, and a processor for resolving the concentrations of the target gases. The device may include an indicator for communicating the concentrations of the target gases.

In a representative five sensor array of the above device, said first sensor, second sensor, third sensor, fourth sensor, and fifth sensor each independently have an electrode which comprises a metal selected from the group consisting of Pt, a Pd/Ni alloy, a Pd/Cu alloy, a Pd/Ag alloy, a Pt/Ir alloy, a Ni/Cr alloy, Cr, a Pt/Cr alloy and a Pt/Sn alloy, wherein the electrode of each said sensor has a sensitivity response different from the sensitivity response of the electrode of each other said sensor. Preferably, the metal is selected from the group consisting of Pt, a Pd/Ni alloy, a Pd/Cu alloy, a Pd/Ag alloy, a Pt/Ir alloy, and a Pt/Sn alloy.

The electrode of the sensor which is sensitive to ethylene is preferably selected from the group consisting of Pt, a Pt/Sn alloy, a Pd/Ni alloy, and a Pt/Ir alloy. Preferably, each sensor in the device has a sensitivity to at least one gas which is different than the sensitivity of each other said sensor to said at least one gas.

In a preferred embodiment, a device for indicating a fault in an electrical transformer comprises an array of at least a first, a second, a third, a fourth and a fifth metal-insulator-semiconductor diode sensors, wherein said first sensor has an electrode comprising platinum, said second sensor has an electrode comprising a palladium/silver alloy, said third sensor has an electrode comprising a palladium/copper alloy, said fourth sensor has an electrode comprising platinum/iridium, and said fifth sensor has an electrode comprising a platinum/tin alloy. Arrays of other combinations of sensor electrode compositions as exemplified above are suitable for detecting fault gases in an electrical transformer.

The MIS diode sensors described above can be mounted onto a probe and placed in the sample of the fluid to be tested but preferably are mounted in-situ in order to provide the capability for continuously monitoring the condition of the fluid, such as electrical transformer oil within the sealed containment vessel. The electronically connected transducer and microprocessor can be mounted outside the containment vessel for protection from the oil and for easy access.

The MIS diode sensors described above can also be used to detect and analyze the concentration of hydrogen, carbon monoxide, alkenes such as ethylene, and alkynes such as acetylene in mixtures of gases or fluids such as chemical process feed, product or waste streams.

Inasmuch as the present invention is subject to variations, modifications and changes in detail, a number of which have been expressly stated herein, it is intended that all matter described throughout this entire specification or shown in the accompanying drawings be interpreted as illustrative and not in a limiting sense. It should thus be evident that a device constructed according to the concept of the present invention, and reasonably equivalent thereto, will accomplish the objects of the present invention and otherwise substantially improve the art of monitoring the concentration of selected liquid or gaseous fluids.

What I claim is:

1. A metal-insulator-semiconductor diode sensor having an electrode consisting essentially of an alloy of platinum and iridium for detecting components in a fluid.

2. The metal-insulator-semiconductor diode sensor as in claim 1 wherein the atomic percent of iridium is about 5% to about 90%.

3. The metal-insulator-semiconductor diode sensor as in claim 1 wherein the atomic percent of iridium is about 30%.

4. A metal-insulator-semiconductor diode sensor having an electrode comprising an alloy of platinum and tin for detecting components in a fluid.

5. The metal-insulator-semiconductor diode sensor as in claim 4 wherein the atomic percent of tin is about 5% to about 80%.

6. The metal-insulator-semiconductor diode sensor as in claim 4 wherein the atomic percent of tin is about 50%.

7. A metal-insulator-semiconductor diode sensor for detecting ethylene, said sensor having an electrode consisting essentially of a composition selected from the group consisting of platinum/tin alloy, platinum/iridium alloy, palladium/nickel alloy, and mixtures thereof.

8. A method for detecting ethylene in a fluid utilizing a metal-insulator-semiconductor diode sensor comprising:
providing said sensor having an electrode consisting essentially of a composition selected from the group consisting of platinum, platinum/iridium alloy, platinum/tin alloy, palladium/nickel alloy, and mixtures thereof,
contacting the electrode with the fluid, and measuring the sensitivity of the electrode to ethylene.

9. The method of claim 8 wherein the fluid is an oil phase fluid.

10. The method of claim 8 including providing said sensor within an array of metal-insulator-semiconductor diode sensors.

11. A device for indicating a fault in an electrical transformer containing a fluid wherein the fault is indicated by a concentration of at least one target gas in the transformer fluid, comprising an array of a plurality of metal-insulator-semiconductor diode sensors having electrodes, wherein the electrode of a first sensor has a first sensitivity to a first target gas and wherein said first sensitivity is different than sensitivities of the first sensor to other target gases in the transformer fluid.

12. The device as in claim 11 wherein the sensitivity of at least one sensor to said first target gas is different than the sensitivities of other electrodes in the array to said first target gas.

13. The device as in claim 12 wherein said at least one sensor is the first sensor.

14. The device as in claim 11, wherein each said sensor has a sensitivity to at least one target gas which is different than the sensitivity of each other said sensor to said at least one target gas.

15. The device as in claim 11 wherein the electrodes of the sensors in the array have varying sensitivities to the target gases which comprise carbon monoxide, hydrogen, ethylene, acetylene and mixtures thereof.

16. The device as in claim 15, wherein the electrode of the sensor having maximum sensitivity to ethylene is selected from the group consisting of Pt, a Pt/Sn alloy, a Pd/Ni alloy, and a Pt/Ir alloy.

17. The device of claim 11 wherein said sensors each independently have an electrode which consisting essentially of a metal selected from the group consisting of Pt, Ir, a Pd/Ni alloy, a Pd/Cu alloy, a Pd/Ag alloy, a Pt/Ir alloy, a Ni/Cr alloy, Cr, a Pt/Cr alloy and a Pt/Sn alloy, wherein the electrode of each said sensor has a sensitivity response different from the sensitivity response of the electrode from each other said sensor.

18. The device of claim 17 wherein said metal is selected from the group consisting of Pt, a Pd/Ni alloy, a Pd/Cu alloy, a Pd/Ag alloy, a Pt/Ir alloy, and a Pt/Sn alloy.

19. The device as in claim 11, further comprising a circuit for determining the magnitude of flat-band voltage of each sensor in response to the presence of the target gas.

20. The device as in claim 19, further comprising a processor for resolving the concentration of individual target gases.

21. The device as in claim 20, further comprising an indicator for communicating the concentrations of the target gases.

22. The device as in claim 11, including a temperature reference electrode.

23. The device as in claim 22, wherein the electrode metal consists essentially of nickel.

24. A device for indicating a fault in an electrical transformer comprising an array of at least a first, a second, a third, a fourth and a fifth metal-insulator-semiconductor diode sensors, wherein the sensors each independently have an electrode which comprises a metal selected from the group consisting of platinum, iridium, palladium/silver alloy, palladium/copper alloy, platinum/iridium alloy, platinum/tin alloy, and palladium/nickel alloy.

25. The device as in claim 24 wherein said first sensor has an electrode comprising platinum, said second sensor has an electrode comprising a first palladium/nickel alloy, said third sensor has an electrode comprising a second palladium/nickel alloy having a different atomic percent nickel than said first palladium/nickel alloy, said fourth sensor has an electrode comprising platinum/iridium, and said fifth sensor has an electrode comprising a platinum/tin alloy.

26. The device as in claim 24 wherein said first sensor has an electrode comprising platinum, said second sensor has an electrode comprising a palladium/silver alloy, said third sensor has an electrode comprising a palladium/copper alloy, said fourth sensor has an electrode comprising a platinum/iridium alloy, and said fifth sensor has an electrode comprising a platinum/tin alloy.

27. The device as in claim 24 wherein said first sensor has an electrode comprising platinum, said second sensor has an electrode comprising a palladium/silver alloy, said third sensor has an electrode comprising a palladium/nickel alloy, said fourth sensor has an electrode comprising a platinum/iridium alloy, and said fifth sensor has an electrode comprising a platinum/tin alloy.

28. The device as in claim 24 wherein said first sensor has an electrode comprising platinum, said second sensor has an electrode comprising a palladium/nickel alloy, said third sensor has an electrode comprising a palladium/copper alloy, said fourth sensor has an electrode comprising a platinum/iridium alloy, and said fifth sensor has an electrode comprising a platinum/tin alloy.

29. The device as in claim 24 wherein said first sensor has an electrode comprising platinum, said second sensor has an electrode comprising a first palladium/silver alloy, said third sensor has an electrode comprising a second palladium/silver alloy having a different sensitivity response than said first palladium/silver alloy, said fourth sensor has an electrode comprising platinum/iridium, and said fifth sensor has an electrode comprising a palladium/copper alloy.

30. The device as in claim 24 wherein said first sensor has an electrode comprising platinum, said second sensor has an electrode comprising a first palladium/silver alloy, said third sensor has an electrode comprising a second palladium/silver alloy having a different sensitivity response than said first palladium/silver alloy, said fourth sensor has an electrode comprising platinum/tin, and said fifth sensor has an electrode comprising a palladium/copper alloy.

31. The device as in claim 24 wherein said first sensor has an electrode comprising platinum, said second sensor has an electrode comprising a palladium/silver alloy, said third sensor has an electrode comprising a palladium/copper alloy, said fourth sensor has an electrode comprising a palladium/nickel alloy, and said fifth sensor has an electrode comprising a platinum/tin alloy.

32. The device as in claim 24 wherein said first sensor has an electrode comprising platinum, said second sensor has an electrode comprising a palladium/nickel alloy, said third sensor has an electrode comprising a palladium/copper alloy, said fourth sensor has an electrode comprising a platinum/iridium alloy, and said fifth sensor has an electrode comprising a palladium/silver alloy.

33. A method for detecting at least one component in a fluid utilizing the metal-insulator-semiconductor diode sensor as in claim 1, wherein said at least one component is selected from the group consisting of carbon monoxide, hydrogen, acetylene, ethylene and mixtures thereof, comprising:

providing said sensor having an electrode consisting essentially of an alloy of platinum and iridium, contacting the electrode with the fluid, and measuring the sensitivity of the electrode to said at least one component in the fluid.

34. The method of claim 33 wherein the fluid is an oil phase fluid.

35. The method of claim 33 including providing said sensor within an array of metal-insulator-semiconductor diode sensors.

* * * * *